US005725867A

United States Patent [19]

Mixon

[11] Patent Number: 5,725,867
[45] Date of Patent: Mar. 10, 1998

[54] ANTIMICROBIAL GLOVES AND A METHOD OF MANUFACTURE THEREOF

[75] Inventor: Grover C. Mixon, Kingstree, S.C.

[73] Assignee: Phoenix Medical Technology, Inc., Andrews, S.C.

[21] Appl. No.: 239,880

[22] Filed: May 9, 1994

[51] Int. Cl.⁶ .................................................. A01N 25/34
[52] U.S. Cl. ........................................... 424/402; 424/404
[58] Field of Search ................................. 424/402, 404; 427/2; 523/122

[56] References Cited

U.S. PATENT DOCUMENTS

| | | | |
|---|---|---|---|
| 3,755,224 | 8/1973 | Lutz, Jr. ........................... | 260/23 |
| 4,603,152 | 7/1986 | Laurin et al. ..................... | 604/265 |
| 5,069,907 | 12/1991 | Mixon et al. ..................... | 424/445 |
| 5,089,205 | 2/1992 | Wu-Nan Huang et al. ....... | 264/255 |
| 5,091,442 | 2/1992 | Milner ............................... | 523/122 |
| 5,261,421 | 11/1993 | Milner ............................... | 128/898 |
| 5,335,373 | 8/1994 | Dangman et al. ................ | 2/161 |

OTHER PUBLICATIONS

*Plastics Engineering Handbook*, p. 402. Society of the Plastics Industry, Inc., 1976.

*Primary Examiner*—Thurman K. Page
*Assistant Examiner*—Sharon Howard
*Attorney, Agent, or Firm*—Rogers & Killeen

[57] ABSTRACT

Antimicrobial protection may be provided to protective gloves by mixing an antimicrobial agent in a glove material plastisol so that the antimicrobial agent migrates to the exposed surfaces of the gloves when the agent on the glove surface has been depleted. Antimicrobial gloves suitable for use in the food industry may be manufactured using a cold dip process with a plastisol that includes the following weight percentages of (a) a polymer resin, such as polyvinyl chloride (PVC), polypropylene polyethylene (PE), or polyurethane, 43 to 53%, (b) a plasticizer, such as DINP, 43 to 53%, (c) a stabilizer, such as CaZn, 2.7 to 4.7%, and (d) triclosan (2,4,4'-trichloro-2'-hydroxydiphenyl ether), 0.3 to 1.0%.

7 Claims, No Drawings

ANTIMICROBIAL GLOVES AND A METHOD OF MANUFACTURE THEREOF

BACKGROUND OF THE INVENTION

The present invention relates to antimicrobial gloves and a method of manufacturing such gloves, and more particularly to antimicrobial gloves for food handlers that are made of triclosan and polyvinyl chloride (PVC), where the gloves are formed by cold dipping glove molds in a plastisol of PVC, triclosan, a plasticizer and a stabilizer.

The food industry is concerned about bacterial contamination and workers in the industry are frequently required to wear protective gloves to reduce the likelihood that the bacteria from their hands will be transmitted to food. However, the protective gloves may pick up contaminating bacteria from food or work surfaces they touch, thereby significantly reducing the effectiveness of the gloves the longer they are worn. A solution, albeit a costly one, is to have the workers change or disinfect their gloves frequently. The food industry would prefer a more workable and cost effective solution.

The gloves used by the food industry are typically made of polyvinyl chloride (PVC), are seamless to reduce the risk of seam failure, and meet federal standards for thickness, strength, elasticity, deformation, etc. Gloves of other materials have been tried, but they either do not meet the federal standards or are not acceptable to the food industry (e.g., high cost, not seamless, difficult to don and remove, uncomfortable to wear, etc.).

Seamless PVC gloves are typically made by dipping glove molds in a low viscosity PVC plastisol (a liquid mixture of the glove material that gels to form the gloves), and machines for dipping the glove molds are well known in the art.

Antimicrobial agents are well known and it would be desirable to provide protective gloves used in the food industry with an antimicrobial agent that provides long lasting protection. However, the industry had been unable to find an antimicrobial agent that meets federal standards for food handling, that can be used with PVC gloves, and that will effectively reduce the risk of bacterial contamination during prolonged wear of the gloves carrying the agent. For example, conventional PVC gloves may be dusted with an antimicrobial agent, but the agent would not be effective for prolonged periods because it would rub off during use and disappear completely when the gloves are immersed in water.

A potential solution is to mix an antimicrobial agent into a plastisol. For example, U.S. Pat. No. 5,091,442 issued Feb. 25, 1992 to Milner suggests that an antimicrobial agent, such as triclosan, may be mixed with a natural rubber latex plastisol to provide antimicrobial protection for a tubular article such as a condom or catheter. However, the effectiveness of the antimicrobial agent in the article will still diminish during use because the agent will gradually disappear from the surface of the article and will not be replenished. That is, the triclosan will be removed from the surface of the natural rubber latex long before the latex wears down to expose the triclosan in the interior thereof. The nature of the natural rubber latex prevents the antimicrobial agent from migrating to the exposed surface of the latex from its interior. This limitation may be acceptable where the article makes a single contaminating contact, but is not acceptable for gloves that will have numerous contacts with diverse potential contaminants.

The Milner patent mentions that PVC may be used instead of the natural rubber latex, but does not suggest how this is to be done. The method disclosed relates only to natural rubber latex, and the differences between latex and PVC preclude the application of the disclosed method to PVC.

It has also been suggested that an antimicrobial agent may be added to a plastic or polymeric film material, such as PVC, that is used to make a surgical drape sheet. The structure of the PVC allows some antimicrobial agents to migrate to the exposed surface of the drape from the interior thereof when the agent has been removed from the surface (see U.S. Pat. No. 5,069,907 issued Dec. 3, 1991 to Mixon, et al.). However, the process and the plastisol used therewith for making a sheet of plastic or polymeric material are not suitable for dipping gloves. In the sheet making process a high viscosity paste is extruded through a sheet feeder at high temperature. As discussed above, the glove dipping process uses a low viscosity plastisol.

Accordingly, it is an object of the present invention to provide novel protective gloves and a method of making protective gloves that obviate the problems of the prior art.

It is another object of the present invention to provide novel protective gloves and a method of providing antimicrobial protection to such gloves in which an antimicrobial agent in the glove material migrates to the exposed surfaces of the gloves when the agent at the glove surface has been depleted.

It is yet another object of the present invention to provide a novel method of making seamless protective gloves for the food industry from a plastisol that includes triclosan and PVC.

It is still another object of the present invention to provide a novel method of making protective gloves in which triclosan antimicrobial agent is mixed with a PVC plastisol before the gloves are formed by a cold dip process whereby the triclosan migrates to the exposed surfaces of the gloves when the triclosan at the surface has been depleted.

These and many other objects and advantages of the present invention will be readily apparent to one skilled in the art to which the invention pertains from a perusal of the claims, the appended drawings, and the following detailed description of preferred embodiments.

DESCRIPTION OF PREFERRED EMBODIMENTS

Antimicrobial protection may be provided to protective gloves by mixing an antimicrobial agent with a glove material plastisol, the agent and plastisol being selected so that the antimicrobial agent migrates to the exposed surfaces of the gloves when the agent at the glove surface has been depleted.

The antimicrobial agent is preferably triclosan and the glove material plastisol preferably includes a polymer, such as PVC, polypropylene polyethylene (PE), or polyurethane. The plastisol preferably includes 43 to 53% polymer by weight and 0.3 to 1.0% triclosan by weight.

Triclosan (2,4,4'-trichloro-2'-hydroxydiphenyl ether) is a broad spectrum antimicrobial agent that is commercially available under the name Microban™ (Clinitex Corp.) and is suitable for use in the food industry.

Antimicrobial gloves suitable for use in the food industry may be manufactured using a cold dip process with a plastisol that includes the following weight percentages of (a) a PVC resin, 43 to 53%, (b) a plasticizer, 43 to 53%, (c) a stabilizer, 2.7 to 4.7%, and (d) triclosan, 0.3 to 1.0%.

The plasticizer may be any suitable product that has been approved for use in the food industry, such as di-isonoyphthalate (DINP). Other phthalate ester plasticizers, such as DIOP, DEOP and DEHP, may be used for other glove applications where use of the plasticizer has not been restricted. The stabilizer may be any suitable product that has been approved for use in the food industry, such as CaZn.

In a preferred embodiment, the plastisol includes 48% PVC resin (weight percentage), 48% DINP plasticizer, 3.7% CaZn stabilizer, and 0.3% triclosan.

In another embodiment the polymer is polypropylene polyethylene (PE). Test results indicate that the effectiveness of the antimicrobial agent is improved when mixed with a PE plastisol because the agent migrates to the surface of the gelled PE plastisol more quickly. PE gloves may find significant applications in a number of areas, although at present the cost may be high for use in the food industry.

The gloves may be formed using a conventional cold dipping process, such as described in *Plastics Engineering Handbook*, page 402 (Society of the Plastics Industry, Inc., 1976). As explained therein, in a cold dipping process a cold or room temperature mold is dipped into a plastisol, removed from the plastisol and fused. The thickness of the coating depends upon the low-shear-rate viscosity and the yield value of the plastisol. The viscosity and yield value of the plastisol are desirably balanced so that the plastisol flows well enough to form a uniform coating and yet does not drip. The plastisol disclosed herein provides a viscosity and yield value balance suitable for making protective gloves.

Conventional mechanical dipping devices may be used. For example, multiple glove forms (e.g., thousands of glove forms) may be carried by a conveyor through the stages in the cold dip process.

In a preferred embodiment, the glove forms may be cold dipped into the plastisol when the forms are about 30° C. warmer than the plastisol, the plastisol being at about 32° C. The gloves remain in the plastisol for about 15 seconds and are thereafter removed and cured by heating to about 240° C. for about five minutes. The cured gloves are cooled at about 66° C. for about fifteen minutes, and thereafter removed from the forms. The glove material is about 0.127 millimeters thick and the gloves are suitable for use in a variety of applications.

The gloves provide effective antimicrobial protection for gloves for the food industry, meeting all applicable federal regulations. During use, as the antimicrobial agent at the surface of the material wears off, the agent in the material migrates to the surface to provide continued protection.

While preferred embodiments of the present invention have been described, it is to be understood that the embodiments described are illustrative only and the scope of the invention is to be defined solely by the appended claims when accorded a full range of equivalence, many variations and modifications naturally occurring to those skilled in the art from a perusal hereof.

What is claimed is:

1. An antimicrobial protective glove having an antimicrobial agent homogeneously distributed in a material from which the glove is formed, and in which the agent migrates to the exposed surface of the glove to restore the antimicrobial effect when the agent at the exposed surface has been removed, the glove material comprising by weight percent:

polyvinyl chloride, 48%;
   a plasticizer, 48%;
   a stabilizer, 3.7%; and
   triclosan, 0.3%.
   wherein said triclosan internal to the glove material will migrate to the surface of the glove when said triclosan at the surface of the glove is removed.

2. The glove of claim 1 wherein said plasticizer is DINP.
3. The glove of claim 1 wherein said stabilizer is CaZn.
4. The glove of claim 1 wherein said glove is seamless.
5. An antimicrobial protective glove having an antimicrobial agent homogeneously distributed in a material from which the glove is formed, and in which the agent migrates to the exposed surface of the glove to restore the antimicrobial effect when the agent at the exposed surface has been removed, the glove material comprising by weight percent:

polyvinyl chloride, 43 to 53%;
   DINP plasticizer, 43 to 53%;
   CaZn stabilizer, 2.7 to 4.7%; and
   triclosan, 0.3 to 1.0%.
   wherein said triclosan internal to the glove material will migrate to the surface of the glove when said triclosan at the surface of the glove is removed.

6. The glove of claim 5 wherein the weight percentages are:

said polyvinyl chloride, 48%;
   said DINP plasticizer, 48%;
   said CaZn stabilizer, 3.7%; and
   said triclosan, 0.3%.

7. The glove of claim 6 wherein said glove is seamless.

* * * * *